(12) United States Patent
DiBiasi

(10) Patent No.: US 9,468,712 B2
(45) Date of Patent: Oct. 18, 2016

(54) PEN NEEDLE DISPENSING APPARATUS

(71) Applicant: Becton, Dickinson and Company, Franklin Lakes, NJ (US)

(72) Inventor: Michael A. DiBiasi, Pompton Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/929,207

(22) Filed: Oct. 30, 2015

(65) Prior Publication Data

US 2016/0051772 A1 Feb. 25, 2016

Related U.S. Application Data

(63) Continuation of application No. 13/198,564, filed on Aug. 4, 2011, now Pat. No. 9,186,452.

(60) Provisional application No. 61/344,541, filed on Aug. 16, 2010.

(51) Int. Cl.
| | |
|---|---|
| *A61M 5/00* | (2006.01) |
| *A61M 5/34* | (2006.01) |
| *A61M 5/32* | (2006.01) |
| *B65D 83/02* | (2006.01) |

(52) U.S. Cl.
CPC ............ *A61M 5/002* (2013.01); *A61M 5/008* (2013.01); *A61M 5/3202* (2013.01); *A61M 5/3204* (2013.01); *A61M 5/3213* (2013.01); *A61M 5/347* (2013.01); *B65D 83/02* (2013.01); *A61M 5/34* (2013.01)

(58) Field of Classification Search
CPC .. A61M 5/3204; A61M 5/002; A61M 5/347; A61M 5/3213; A61M 5/008; A61M 5/34; A61M 5/3202; B65D 83/02
See application file for complete search history.

(56) References Cited

U.S. PATENT DOCUMENTS

| | | | |
|---|---|---|---|
| 2,966,986 A * | 1/1961 | Jones | A61M 5/002 206/365 |
| 3,825,002 A | 7/1974 | Paige | |
| 4,892,525 A * | 1/1990 | Hermann, Jr. | A61M 5/3213 206/365 |
| 5,545,145 A | 8/1996 | Clinton et al. | |
| 5,968,021 A | 10/1999 | Ejlersen | |
| 6,159,193 A | 12/2000 | Turk | |
| 6,921,383 B2 | 7/2005 | Vitello | |

(Continued)

FOREIGN PATENT DOCUMENTS

| | | | |
|---|---|---|---|
| DE | EP 2201976 A1 * | 6/2010 | A61M 5/002 |
| EP | 0916355 A2 | 5/1999 | |

(Continued)

*Primary Examiner* — Emily Schmidt
*Assistant Examiner* — Lauren M Peng
(74) *Attorney, Agent, or Firm* — Dickinson Wright PLLC

(57) ABSTRACT

An apparatus is disclosed for storing and dispensing a pen needle for an injection device, including a packaging assembly including a pliable outer cover, the outer cover having a hub portion, a needle portion disposed at a distal end of the hub portion, and a flange disposed at a proximal end of the hub portion, the hub portion having internally protruding splines or other structures for engaging a hub of a pen needle. The hub portion is sufficiently pliable for a user to press gripping portions of the hub portion so that corresponding internal portions of the hub portion between the splines contacts the pen needle hub to increase a surface area contact between the outer cover and a pen needle therein.

4 Claims, 9 Drawing Sheets

(56) References Cited

U.S. PATENT DOCUMENTS

| 8,231,602 B2 | 7/2012 | Anderson et al. |
|---|---|---|
| 2003/0121812 A1 | 7/2003 | Sprieck et al. |
| 2010/0063457 A1 | 3/2010 | Crossman |
| 2010/0185178 A1 | 7/2010 | Sharp et al. |
| 2012/0022460 A1 | 1/2012 | Horvath et al. |
| 2012/0029440 A1 | 2/2012 | Boyd et al. |

FOREIGN PATENT DOCUMENTS

| EP | 2201976 A1 | 6/2010 |
|---|---|---|
| GB | 2437923 B | 11/2011 |
| JP | 11137687 | 5/1999 |
| JP | 2000262616 A | 9/2000 |
| WO | WO-2010072695 A1 | 7/2010 |
| WO | WO-2010090734 A1 | 8/2010 |
| WO | WO-2011146042 A1 | 11/2011 |

* cited by examiner

PEN NEEDLE DISPENSING APPARATUS

CROSS-REFERENCE TO RELATED APPLICATIONS

This application is a continuation of U.S. patent application Ser. No. 13/198,564, filed on Aug. 4, 2011, which claims the benefit of U.S. Provisional Patent Application Ser. No. 61/344,541, filed on Aug. 16, 2010, the disclosures of both of said prior applications being incorporated herein by reference in their entirety.

BACKGROUND OF THE INVENTION

1. Field of the Invention

The present invention relates to needles for a pen injection device, and more particularly, to an apparatus for dispensing and storing needles for a pen injection device.

2. Description of the Related Art

Medication delivery pens are used for self-injection of precisely measured doses of medication. Pens are widely used, for example, by diabetics to self-inject insulin. A typical medication delivery pen includes a cartridge which contains a volume of liquid medication sufficient for several doses. Using a pen needle attached to the pen device, the dose is injected into a tissue area, such as the intramuscular tissue layer, the subcutaneous tissue layer, or the intradermal tissue layer.

The assembly and operation of a typical pen injection device is described in commonly-assigned U.S. Pat. No. 7,645,264, which is hereby incorporated by reference in its entirety.

Pen injection devices, such as an exemplary pen injector 50, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The medicament cartridge 12 is typically a glass tube sealed at 1 end with a septum 16 and at the other end with the stopper 15. In standard drug delivery pens, the dosing and delivery mechanisms are all found within the outer sleeve 13. Those mechanisms are not described in greater detail herein as they are understood by those knowledgeable of the art.

A pen needle assembly 10 includes a hub 20, a patient needle 11 extending from a patient end of the pen needle assembly, and a septum-penetrating needle cannula 18 disposed within the hub 20 on a non-patient side thereof. The septum-penetrating needle cannula 18 is in fluid communication with the patient needle 11. The hub 20 is preferably screwed onto the lower housing 17, although other attachment means can be used such as attaching directly to the medicament cartridge 12. In attaching the hub 20 to the lower housing 17 or medicament cartridge 12, the septum-penetrating cannula 18 pierces the septum 16, but the septum 16 does not move with respect to the medicament cartridge 12. The stopper 15, however, is axially displaceable within the medicament cartridge 12 while maintaining a fluid-tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen injector 50, a rigid outer shield 29 that attaches to the hub 20, covers the hub 20. The outer shield 29 can also be used as a handle or grip to screw hub 20 onto or off of pen injector 50. Typically, a teardrop cover or label 32, attached to a top flange 30 of the outer shield 29 and having a tab 34 for a handle (best shown in FIG. 8), provides a sterility barrier for the contents of the outer shield 29. An inner shield or needle cover 28 covers the patient needle 11 within the outer shield 29. The inner shield 28 can be secured to the hub 20 to cover the patient needle 11 by any suitable means, such as an interference fit or a snap fit. The outer shield 29 and inner shield 28 are removed prior to use. The cap 21 fits snugly against outer sleeve 13 to allow a user to securely carry the pen injection device 50.

Pen needle assemblies are usually sold individually packaged inside a plastic cover (such as outer shield 29) with a label covering the opening in the cover to provide a sterility barrier. These individually packaged pen needle assemblies are often sold packed loosely in a container, such as a box. Boxes of various sizes are used for various quantities of the individually packaged pen needle assemblies (for example, a 50 count box or a 100 count box).

SUMMARY OF EMBODIMENTS OF THE INVENTION

It is an aspect of the present invention to provide an apparatus for storing pen needles. More specifically, it is an aspect of the present invention to provide an apparatus for storing pen needles prior to their use as well as subsequent to their use. Additionally, it is an aspect of the present invention to provide an apparatus for dispensing pen needles for use with a pen injection device.

The foregoing and/or other aspects of the present invention are achieved by providing an apparatus for storing and dispensing a pen needle for an injection device, including a pliable outer covering for storing a pen needle assembly with a sterility barrier having a heat activated adhesive to bond the sterility barrier with the outer covering. The outer covering is sufficiently pliable that a user can compress the outer covering to grasp and hold the pen needle assembly stored within during attachment of the pen needle assembly to the pen injection device.

The foregoing and/or other aspects of the present invention are also achieved by providing an apparatus for storing and dispensing a pen needle for an injection device, including a packaging assembly including a pliable outer cover, the outer cover having a hub portion, a needle portion disposed at a distal end of the hub portion, and a flange disposed at a proximal end of the hub portion, the hub portion having internally protruding structures for engaging a hub of a pen needle. The hub portion is sufficiently pliable for a user to press gripping portions of the hub portion so that corresponding internal portions of the hub portion between the splines contacts the pen needle hub to increase a surface area contact between the outer cover and a pen needle therein.

The foregoing and/or other aspects of the present invention are also achieved by providing a method of storing and dispensing a pen needle for an injection device, the method including the operations of pressing gripping portions of a hub portion of a pliable outer cover having a pen needle therein, so that internal portions of the hub portion contact a hub of the pen needle to increase a surface area of contact between the pen needle and the outer cover. The method also includes attaching the injection device to the hub while pressing the gripping portions, and removing the pen needle from the outer cover.

The foregoing and/or other aspects of the present invention are also achieved by providing a method of packaging a plurality of pen needles for an injection device, the method including providing a plurality of outer covers having needle portions, hub portions, and flanges with separably joined edges in an array, the outer covers having a corresponding plurality of pen needles disposed therein.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which.

DETAILED DESCRIPTION OF EMBODIMENTS OF THE PRESENT INVENTION

Figure 1:
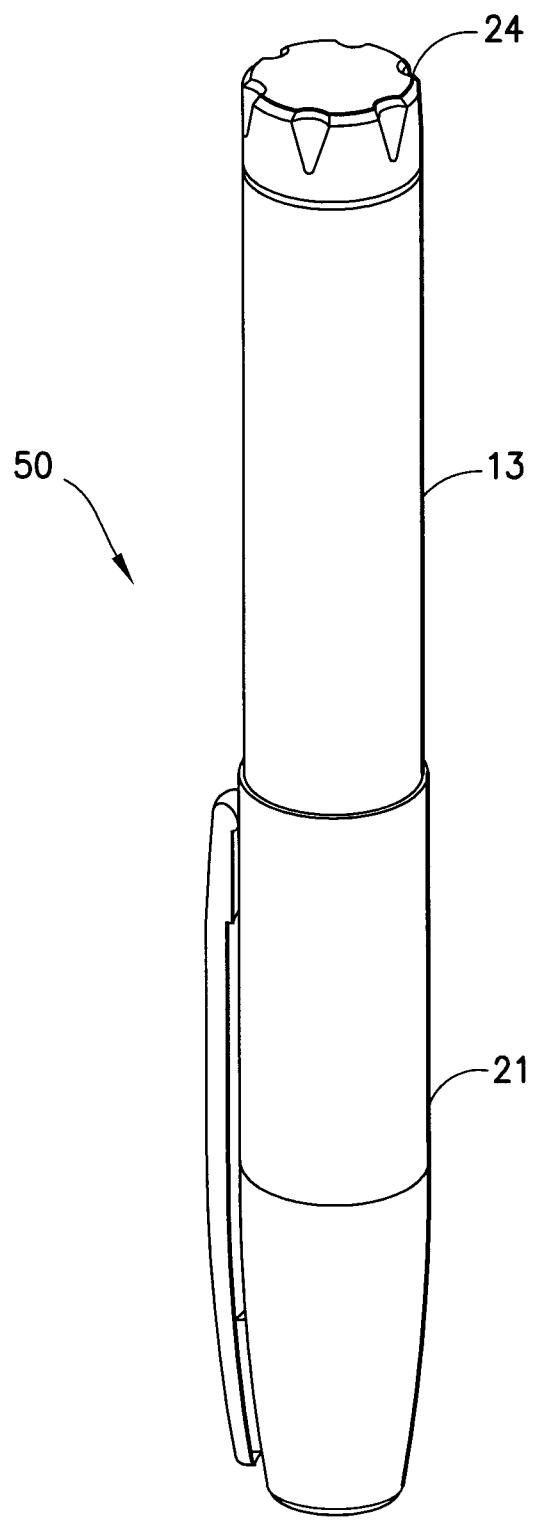
FIG. 1 is a perspective view of an exemplary drug delivery pen.
Figure 2:
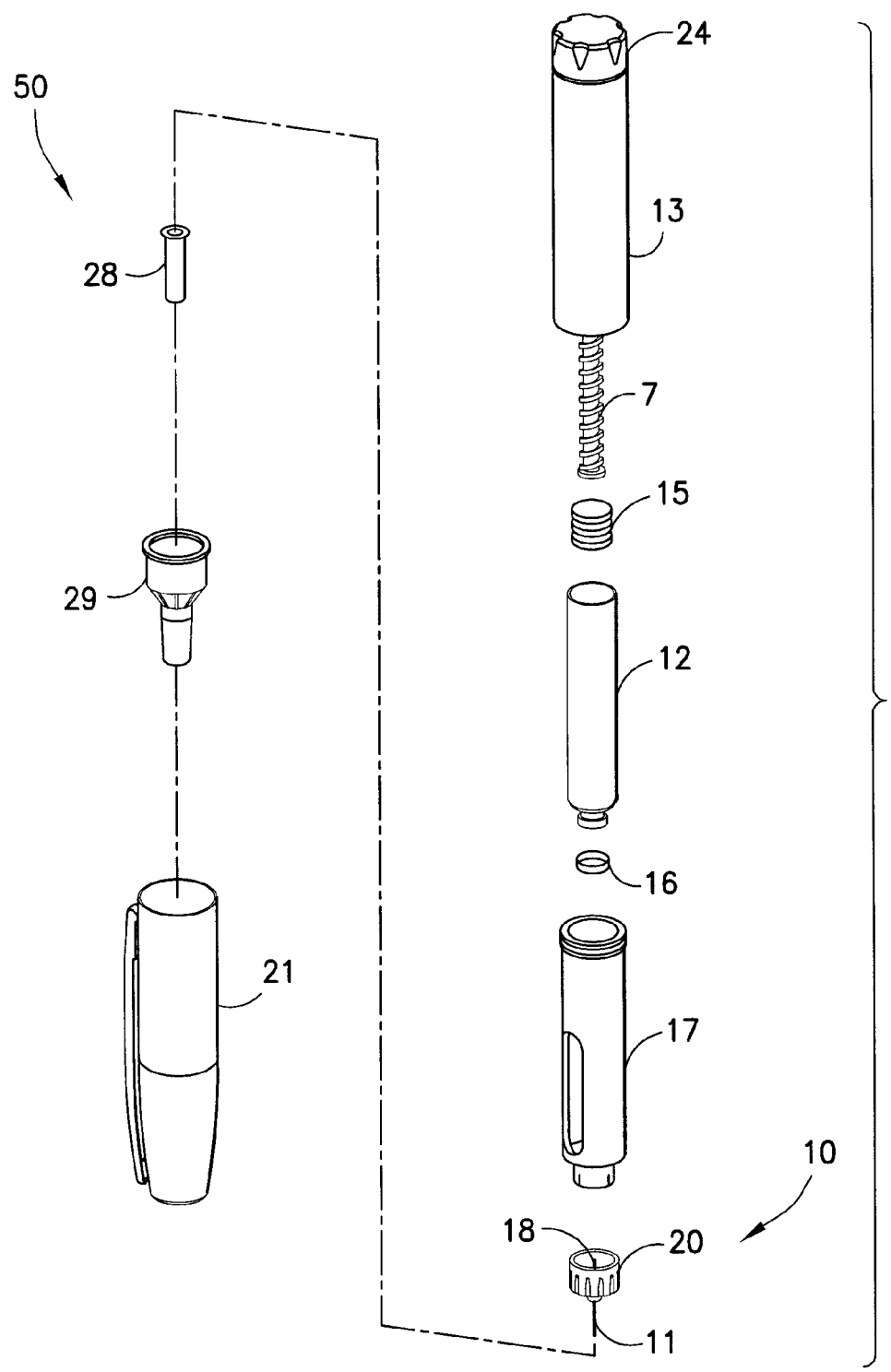
FIG. 2 is an exploded view of the exemplary drug delivery pen of FIG. 1.

Reference will now be made in detail to embodiments of the present invention, examples of which are illustrated in the accompanying drawings, wherein like reference numerals refer to the like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 3:
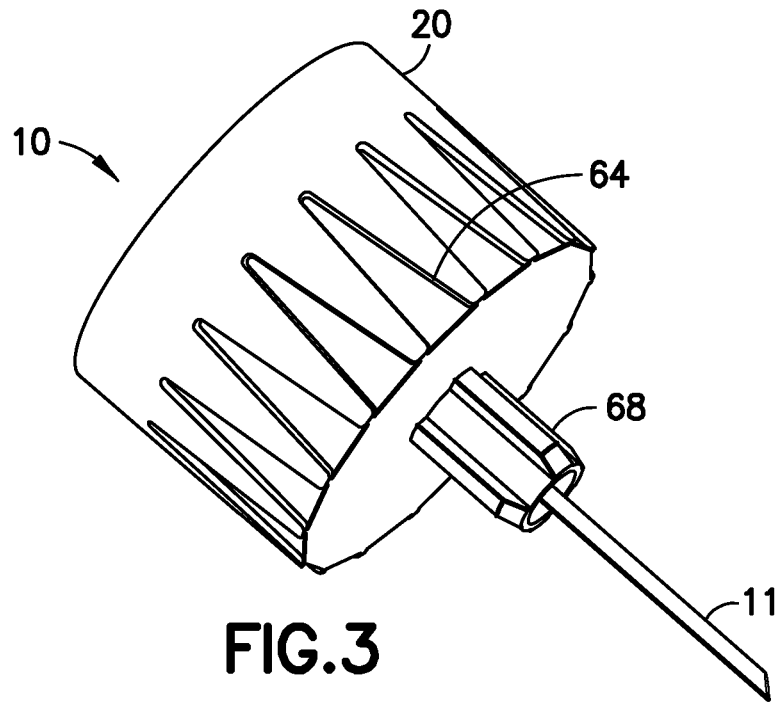
FIGS. 3 and 4 are perspective views of a pen needle assembly in accordance with an embodiment of the present invention.
Figure 4:
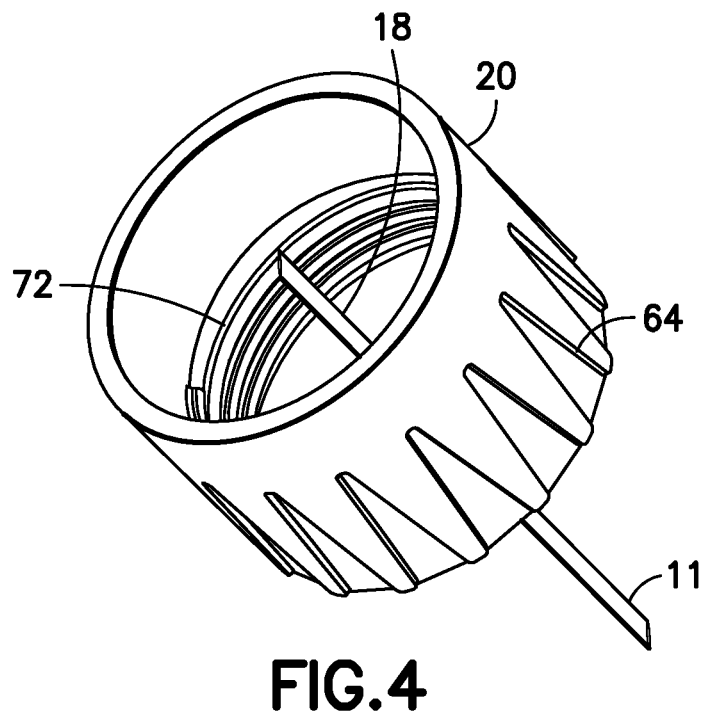

FIGS. 3 and 4 are perspective views of a pen needle assembly 10 in accordance with an embodiment of the present invention. For brevity, the phrase "pen needle 10" will be used hereinafter instead of "pen needle assembly 10." As shown in FIG. 3, the pen needle 10 includes a hub 20 disposed at a non-patient end thereof. The hub 20 includes a plurality of ribs 64 for engagement with anti-rotation/retaining structures that will be described in greater detail below. In addition, protrusion 68 extends from a patient end of the hub 20 and the patient needle 11 extends from the protrusion 68. The septum-penetrating needle cannula 18 (best shown in FIG. 4) disposed within the non-patient end of the hub 20 fluidly communicates with the patient needle 11. Further, as shown in FIG. 4, the interior of the non-patient end of the hub 20 includes threads 72 for connection with an injection device, such as the pen injector 50. For brevity, hereinafter, the pen injector 50 will be employed as an exemplary injection device. One skilled in the art, however, will appreciate that other injection devices may be used without departing from the scope of the present invention.

Figure 5:
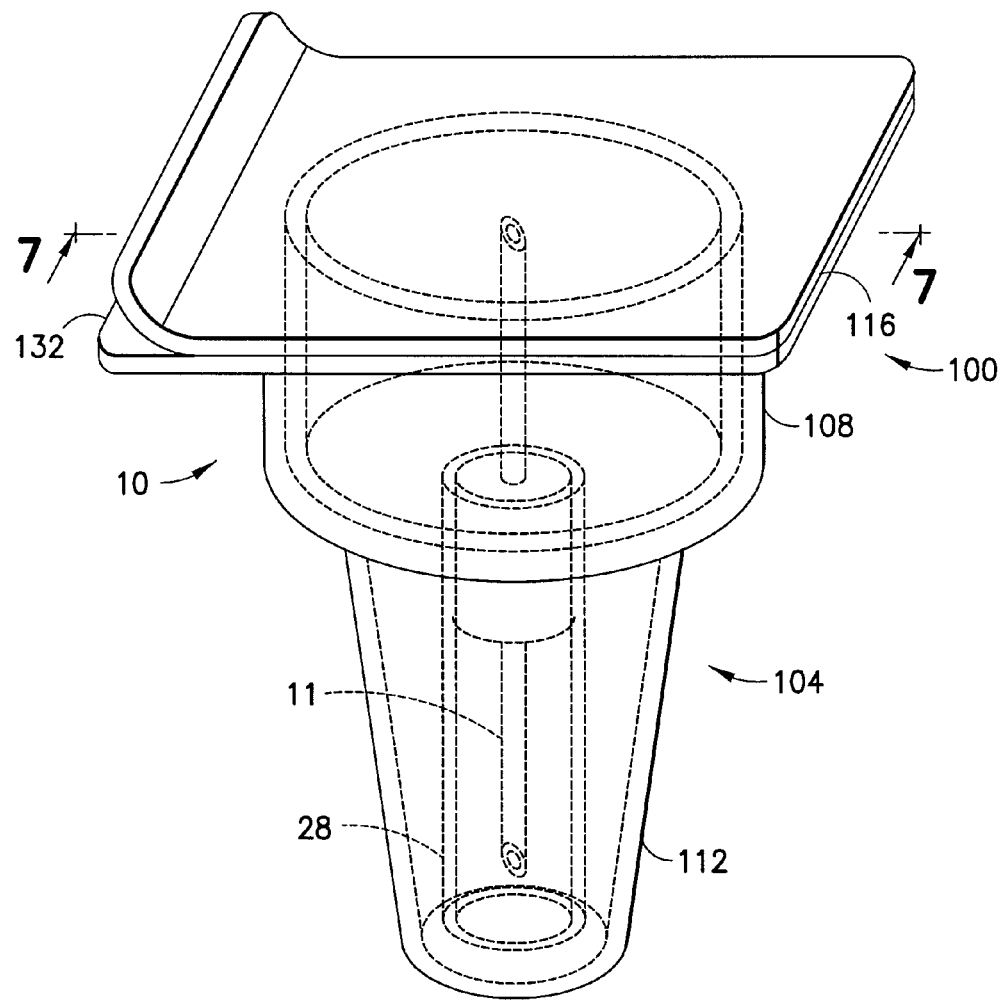
FIG. 5 is a perspective view of a packaging assembly in accordance with an embodiment of the present invention.

FIG. 5 is a perspective view of a packaging assembly 100 in accordance with an embodiment of the present invention. As shown in FIG. 5, a packaging assembly 100 includes a pliable blister-pack or outer cover 104 for storing a pen needle 10 therein. The outer cover 104 includes a hub portion 108 and a needle portion 112. According to one embodiment, the material for the pliable outer cover 104 can be a pliable transparent plastic material, such as standard medical grade PETG copolyester having a thickness in the range of about 0.025" to 0.035" (0.635 mm to 0.890 mm), for example, preferably about 0.030" (0.760 mm). One of ordinary skill in the art will understand that other materials may be used without departing from the scope of the invention. According to one embodiment, as shown in FIG. 5 an inner shield 28 covers a patient needle 11 within the outer cover 104.

The packaging assembly 100 also includes a sterility barrier 116 that is at least partially removable for accessing the pen needle 10. According to one embodiment, the material for the sterility barrier 116 can be surgical grade kraft-paper having a thickness in the range of about 0.005" to 0.020" (0.125 mm to 0.508 mm), for example, preferably 0.013" (0.330 mm). One of ordinary skill in the art will understand that other materials may be used without departing from the scope of the invention.

Figure 6:
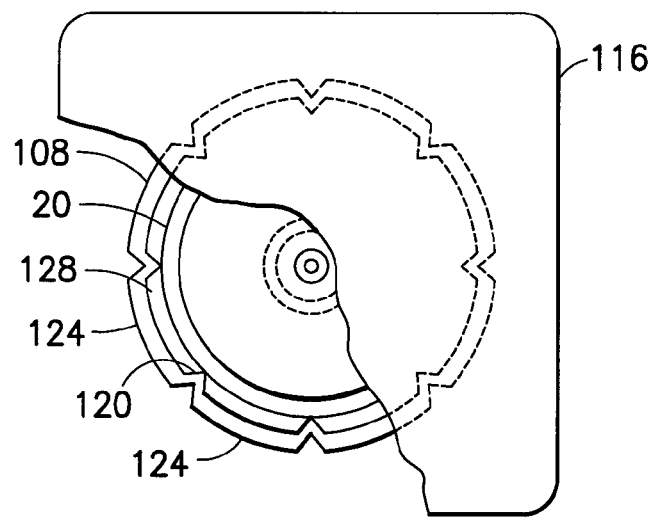
FIG. 6 is a partial plan view of the packaging assembly of FIG. 5.
Figure 7:
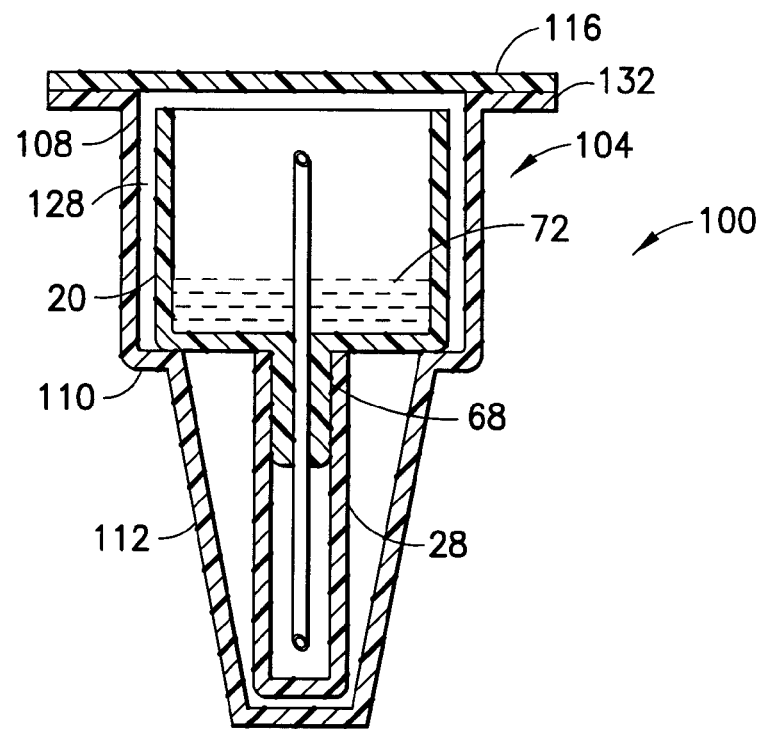
FIG. 7 is a perspective view in cross-section taken along line 7-7 in FIG. 5 of the packaging assembly of FIG. 5.

FIG. 6 is a partial plan view of the packaging assembly 100. FIG. 7 is a perspective view in cross-section taken along line 7-7 in FIG. 5 of the packaging assembly 100. As shown in FIG. 6, the hub portion 108 of the packaging assembly 100 for holding a hub 20 of the pen needle assembly 10 preferably includes a plurality of splines 120 for holding the hub 20 and preventing the pen needle 10 from moving freely within the outer cover 104. These splines may be formed by molding, thermoforming, or other methods. In the embodiment illustrated in FIGS. 6 and 7, the needle portion 112 is substantially frustoconical, the hub portion 108 is substantially cylindrical, and a shoulder portion 110 is disposed between the needle portion 112 and the hub portion 108 for limiting an insertion depth of the pen needle 10.

Additionally, as shown in FIG. 6, adjacent to the splines 120, the hub portion 108 includes a plurality of gripping portions 124. As shown in FIGS. 6 and 7, and as will be described in greater detail below, the gripping portions 124 are spaced apart from the hub 20 such that gaps 128 exist between the gripping portions 124 and the hub 20.

Patients with diabetes, for example, may demonstrate a reduction in tactile abilities of the fingers known as peripheral neuropathy, which may increase in intensity as the disease progresses. This can result in the patient's inability to easily connect the pen needle 10 onto an injection device, such as the pen injector 50. Similarly, peripheral neuropathy may inhibit the patient's ability to easily remove the pen needle 10 from the pen injector 50.

Materials for a typical rigid outer shield 29 include polypropylene (PP) or polyethylene (PE). When attempting to connect a pen needle 10 onto the pen injector 50, the patient typically touches only the rigid, usually opaque, outer shield 29, which may feel slippery to the patient.

In contrast to the outer shield 29, because the outer cover 104 can be significantly more pliable, the outer cover 104 can provide greater tactile feedback for the user, enabling a greater amount of control of the pen needle 10 while the patient connects the pen needle to the pen injector 50. For example, when squeezing the hub portion 108 while turning it, radial torque is transferred directly to the hub 20 by at least the splines 120. Because of the pliability of the hub portion 108, the patient can more easily determine the force required to squeeze the hub portion 108 to prevent rotation of the pen needle 10 when connecting the pen needle 10 to the pen injector 50.

Further, because of the splines 120 and the gaps 128, when the patient grasps and squeezes the gripping portions 124 of the hub portion 108, the splines 120 contact the hub 20 with greater force and internal portions of the pliable hub portion 108 between the splines 120 collapse against the hub 20, increasing the surface area contact between the hub portion 108 and the hub 20. The increase in the surface area contact results in greater frictional resistance between the outer cover 104 and the pen needle 10, thereby allowing the patient to more easily gauge the amount of pressure required to prevent rotational movement of the pen needle 10 with respect to the outer cover 104 when trying to secure the pen needle 10 to the pen injector 50.

Moreover, the pliability of the needle portion 112 offers another advantage over the outer shield 29 if the patient desires to keep the inner shield 28 within the outer cover 104. After securing the pen needle to the pen injector 50, the patient can grasp the inner shield 28 through the needle portion 112 and remove the pen needle 10 while maintaining the inner shield within the outer cover. In contrast, the rigidity of the typical outer shield 29 does not permit such utility.

The patient also experiences an advantage when removing the pen needle 10 from the pen injector 50. Similar to connecting the pen needle 10 and the pen injector 50, when using a typical outer shield 29, the wall of the outer shield 29 is too rigid to be squeezed to any significant extent, causing the patient to rely solely on the fit between the hub 20 and the inner surface of the rigid outer shield 29 to provide the necessary pull force required to pull the septum-penetrating needle cannula 18 from the septum of the medicament cartridge 12. Additionally, the small top flange 30 of the outer shield 29, which is used for label sealing, provides added rigidity to the outer shield 29.

In contrast, the pliable outer cover 104 may be easily squeezed between the patient's fingertips, the force of which is transferred directly from the inside of the outer cover 104 to the hub 20, allowing for easier withdrawal of the septum-penetrating needle cannula 18 from the septum. In other words, when the patient grasps and squeezes the gripping portions 124 of the hub portion 108, the splines 120 contact the hub 20 with greater force and the pliable hub portion 108 collapses against the hub 20, increasing the surface area contact between the hub portion 108 and the hub 20 and providing a more efficient transfer of force from the patient's fingers.

The splines 120 are discrete protruding structures that grip and also serve a spacing function, i.e., to establish gaps 128. One skilled in the art will appreciate that the splines 120 may be replaced by other features, formations, structures, etc. that perform the same functions.

Figure 8:
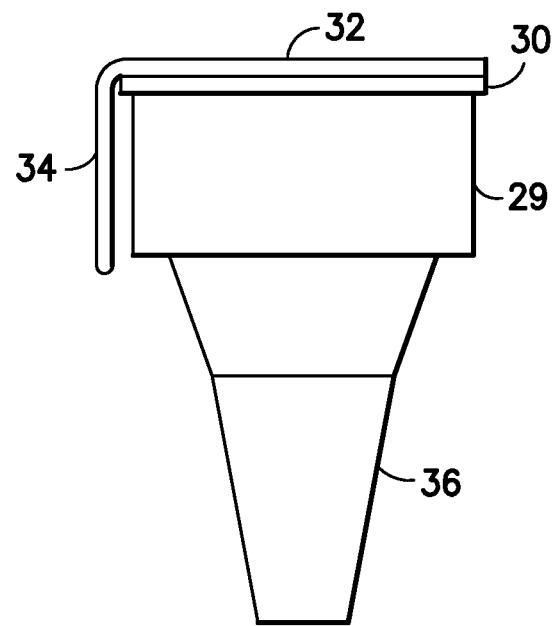
FIG. 8 is a perspective view of a typical outer shield for a pen needle assembly of FIG. 3.
Figure 9:
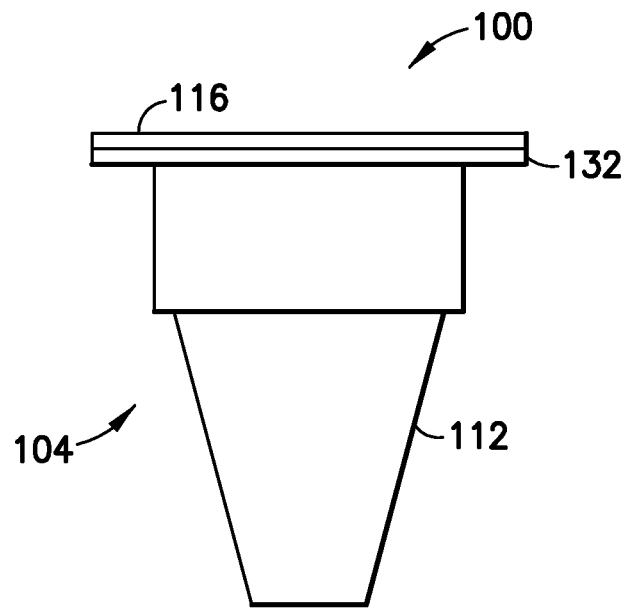
FIG. 9 is a perspective view of the packaging assembly of FIG. 5.

FIG. 8 is a perspective view of a typical outer shield 29 and FIG. 9 is a perspective view of the packaging assembly 100 in accordance with an embodiment of the present invention. As shown in FIGS. 8 and 9, in comparison to the top flange 30 of the outer shield 29, the top flange 132 of the outer cover 104 is preferably much larger. Additionally, as will be discussed in greater detail below, the needle portion 112 of the outer cover 104 is preferably much wider than a needle portion 36 of the outer shield 29.

Patients with reduced tactile abilities can also often experience difficulty in removing the sterility barrier (for example, "teardrop" label 32) from the rigid outer shield 29. A typical teardrop label 32 used as the sterility barrier for the rigid outer shield 29 has a thin polyethylene or polypropylene layer on the underside of the label 32. Under intense heat (for example, 400-440° F. (204-227° C.)), the thin layer on the underside of the label melts onto the flange 30 of the outer shield 29. This plastic to plastic bonding provides a very tenacious grip of the label 32 to the flange 30.

These labels 32 are opened by first pulling on a side tab 34, and then pulling up on the tab 34. In this manner, the patient has to overcome an especially heavy label breakout force at the leading edge of the flange 30, with only the tab 34 to hold onto with one hand and the often slippery PE or PP outer shield 29 with the other. As the label 32 continues to be pulled perpendicularly from the flange 30 and approaches the center of the diameter of the outer shield 29, the required removal force substantially drops. Then, there is a sudden increase in the required removal force as the label 32 approaches the trailing edge of the flange 30. This may cause over-pulling on the part of the patient, which might cause the outer shield 29 to slip out of the patient's grip and result in a loss of sterility of the pen needle 10.

In contrast, blister-pack labels, such as sterility barrier 116, tend to lend themselves to easy removal due to their reliance on heat-activated or pressure-sensitive adhesives. These adhesives, particularly when combined with any number of available label geometry configurations designed specifically for ease of grasping and manipulation, can be a great benefit to patients with reduced tactical abilities preparing for their injections.

In addition, as shown, for example, in FIGS. 6, 7, and 9, the squared-off flange 132 of the outer cover 104 can provide a larger surface area for sealing than the flange 30 of the outer shield 29. The flange 132 also provides the patient with additional area to hold the packaging assembly 100 during label removal and manipulation, as well as pen needle 10 attachment and detachment with respect to the pen injector 50. Further, the flange 132 provides increased patient protection and confidence against accidental needlesticks.

In embodiments of the present invention, a heat-activated or pressure-sensitive adhesive can be used to fasten the sterility barrier 116 to the flange 132 of the outer cover 104. An example of such an adhesive can be any medical grade heat-activated epoxy laminate, of which many formulations are available, including Dow Chemical Company's solution vinyl resin series of the VCAR, VAGH or VMCH types.

Patients with diabetes and other conditions requiring injections sometimes suffer from impaired vision, and subsequent hand/eye coordination issues. According to one embodiment, the outer cover 104 is manufactured from a material providing a high degree of transparency. Accordingly, the patient can more clearly see attachment of the pen needle 10 onto the pen injector 50 through the wall of the outer cover 104. This aids the patient in keeping the central axis of the hub 20 (in other words, the septum-penetrating needle cannula 18) properly aligned with the central axis of the pen injector 50. This clarity not only provides easier targeting of the hub 20 with respect to the pen injector 50, but also helps to prevent the edge of the hub 20 from catching on the edge of the tip of the pen injector 50 during connection with the pen needle 10.

Further, when removing the pen needle 10 from the pen injector 50, the opacity of the outer shield 29 can sometimes contribute to the exposed patient needle 11 accidentally penetrating through needle portion 36 of the outer shield 29, and thus may produce accidental needlesticks. In contrast, the clarity of the outer cover 104 is beneficial in targeting the exposed patient needle 11 into the center of the needle portion 112 of the outer cover 104, thereby reducing the possibility of the patient needle 11 penetrating through the outer cover 104.

Additionally, if the patient maintains the inner shield 28 within the outer cover 104 when removing the pen needle 10 from the outer cover, the clarity of the outer cover aids the patient in fitting the needle 11 into the inner shield 28. Likewise, the pliability of the needle portion 112 can aid the patient. The user can grasp the larger surface area of the needle portion at a distal end thereof, and thereby grip a distal end of the inner shield 28 to maintain the stability of the inner shield 28 when inserting the needle 11 therein. By gripping the distal end of the inner shield, the patient reduces the risk of needlestick during insertion of the needle 11 into the inner shield 28.

Moreover, as shown in FIGS. 8 and 9, the needle portion 112 of the outer cover 104 is wider than the narrow profile of the needle portion 36 of the outer shield 29. Accordingly, with respect to the needle portion 36, the walls of the needle portion 112 are moved outward, further from the needle. This also helps to prevent accidental penetration of the patient needle through the outer cover 104, and thereby helps to protect the patient's fingers from accidental needlesticks.

Furthermore, the increased size of the flange 132 with respect to the flange 30 and the squared configuration of the flange 132 allows the patient's fingers to be farther away from the needle portion 112 during removal of the pen needle 10 from the pen injector 50, and thus further reduces the likelihood of accidental needlesticks. In other words, because of the increased size and the shape of the flange 132, a patient can grasp the outer cover 104 by opposing edges of the rectangular flange 132, or by opposing faces of the flange 132 (for example, in a corner thereof) during the initial insertion of the pen needle 10 into the outer cover 104. Subsequently, the user can grasp the gripping portions 124 of the hub portion 108 to increase the surface area contact between the hub portion 108 and the hub 20 for removal of the pen needle 10 from the pen injector 50.

It is important to the health and safety of each patient that he or she receive pen needles 10 that are free from critical defects, such as an incomplete sterility barrier. The above-described process for heat-sealing the teardrop labels 32 to the flange 30 of the outer shield 29 has tight processing windows, and occasionally delivers weak or incomplete label seals. Although the probability for this to happen is low due to the amount of in-process quality assurance testing that is done during production, the risk of incomplete sterility barriers still exists.

In contrast, the ability of blister packaging to eliminate critical failures due to weak, faulty, or incomplete seals, has long been known to medical device manufacturers, as evidenced by the number of blister packed syringes and other medical devices that have been successfully produced and sold over the years. For example, according to one embodiment, the sealing of the outer cover 104 by the sterility barrier 116 is accomplished using a heat-activated adhesive that is activated at around 140° F. (60° C.). Thus, ensuring the proper conditions for sterile sealing of the outer cover 104 is less demanding than the conditions required for sterile sealing of the outer shield 29. Further, as an additional benefit to the patient, less force is required to break the seal of the adhesive between the sterility barrier 116 and the flange 132 of the outer cover 104 than is required to break the plastic to plastic bond between the teardrop labels 32 and the flange 30 of the outer shield 29.

Figure 10:
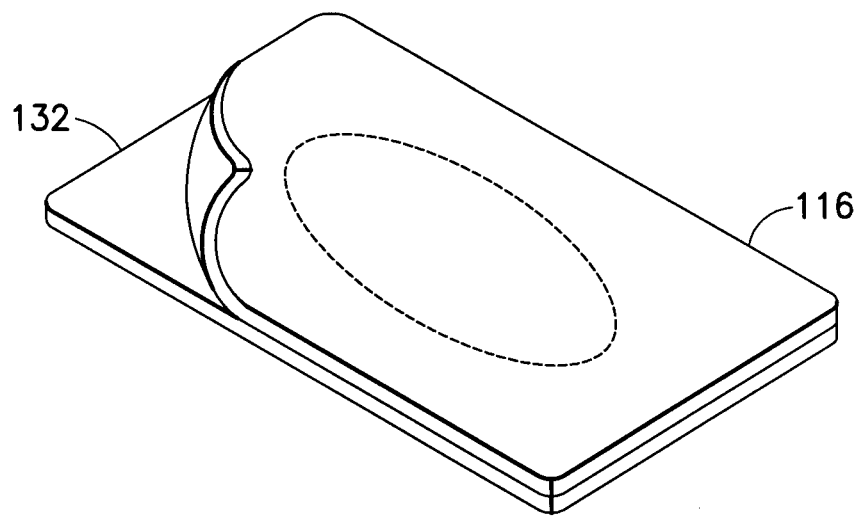
FIG. 10 is a partial perspective view of an alternative sterility barrier configuration for the packaging assembly of FIG. 5.
Figure 11:
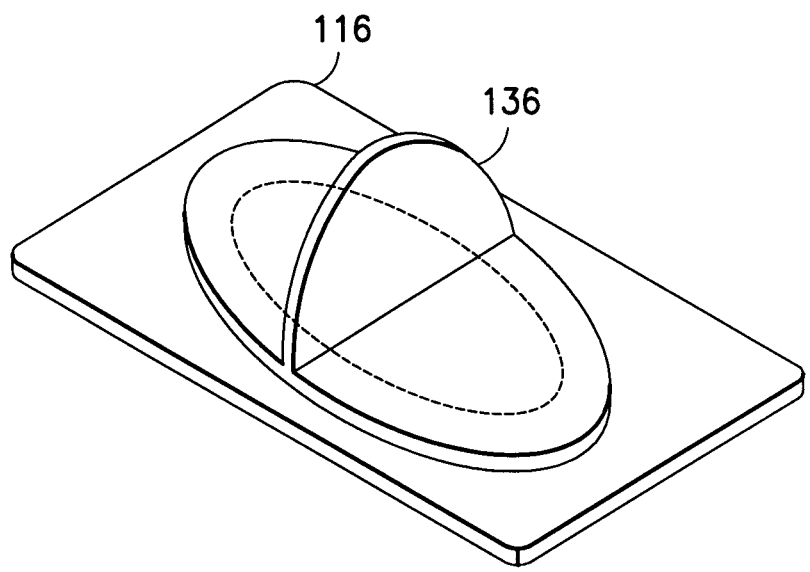
FIG. 11 is a partial perspective view of another alternative sterility barrier configuration for the packaging assembly of FIG. 5.

Referring back to FIG. 5, the illustrated embodiment of the sterility barrier 116 is an edge-peel configuration. In other words, to remove the sterility barrier 116 shown in FIG. 5, the patient lifts one edge of the sterility barrier 116 with respect to the flange 132 of the outer cover 104. Subsequently, the patient peels back the sterility barrier 116 to reveal the non-patient end pen needle 10. FIGS. 10 and 11 are partial perspective views of alternative sterility barrier configurations. In contrast to FIG. 5, FIG. 10 illustrates a corner-peel configuration in which the patient first lifts a corner of the sterility barrier 116. FIG. 11 illustrates a lift and pull configuration. More specifically, the patient first lifts a flap 136 and then, grasping the flap 136 peels back the sterility barrier 116 with respect to the flange 132 to reveal the non-patient end of the pen needle 10.

Figure 12:
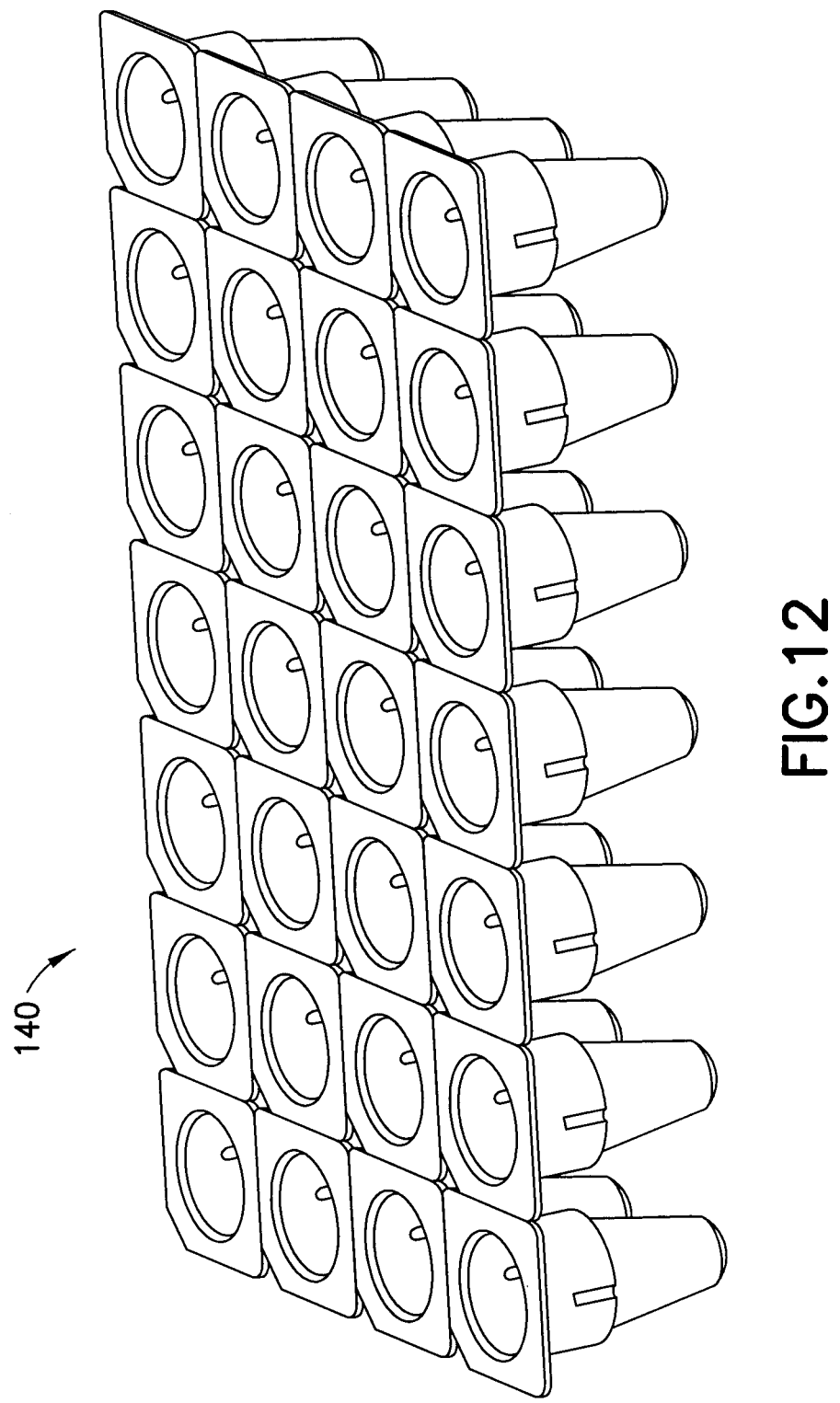
FIG. 12 is a perspective view of a packaging array of a plurality of packaging assemblies of FIG. 5.

FIG. 12 is a perspective view of a packaging array 140 of a plurality of packaging assemblies 100. As shown in FIG. 12, a packaging array 140 is a 4×7 array joining 28 packaging assemblies 100. One of ordinary skill in the art, however, will appreciate arrays of various sizes can be made without departing from the scope of the present invention. In FIG. 12, the respective sterility barriers 116 are removed for illustrative purposes. According to one embodiment, the connection between the individual packaging assemblies 100 is perforated to ease removal of a single packaging assembly 100 or a sub-array of packaging assemblies 100 from adjoining packaging assemblies 100. Although the flange 132 of the illustrated embodiment is a square parallelogram, one skilled in the art will appreciate that other shapes may be used without departing from the scope of the invention. For example, the flange may be diamond-shaped, triangular, rectangular, pentagonal, hexagonal, heptagonal, octagonal, or the like. Preferably, the flange is square, rectangular, hexagonal, or octagonal, so that edges of the flange may be joined to minimize waste and increase packing density. In other words, the flange is preferably shaped to provide a maximum number of packaging assemblies per volume.

In the packaging array 140 shown in FIG. 12, for added convenience to the patient, the pen needles 10 are packaged in blister containers or connected compartments much like typical over-the-counter medications. According to the embodiment shown, up to 28 pen needles may be available on each "card" or "sheet" or packaging array 140. As such, a supply of pen needles may be easily and safely transported by the patient instead of the patient having to carry a shelf carton of loose outer shields 29.

Figure 13:
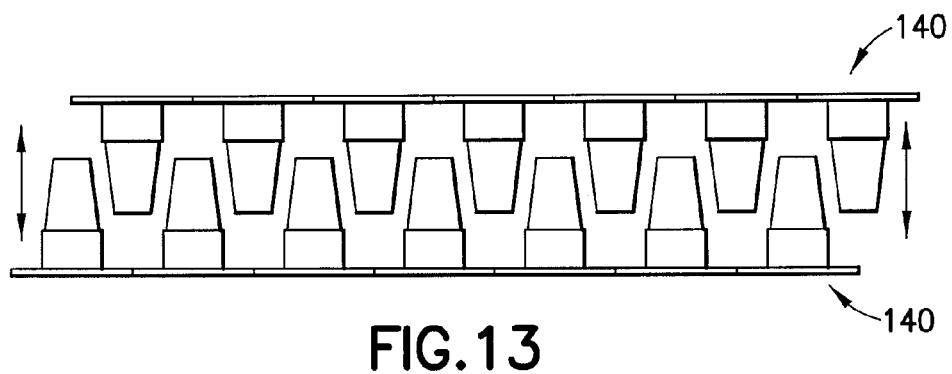
FIGS. 13 and 14 are side elevation views illustrating nesting of a plurality of arrays of FIG. 12.
Figure 14:
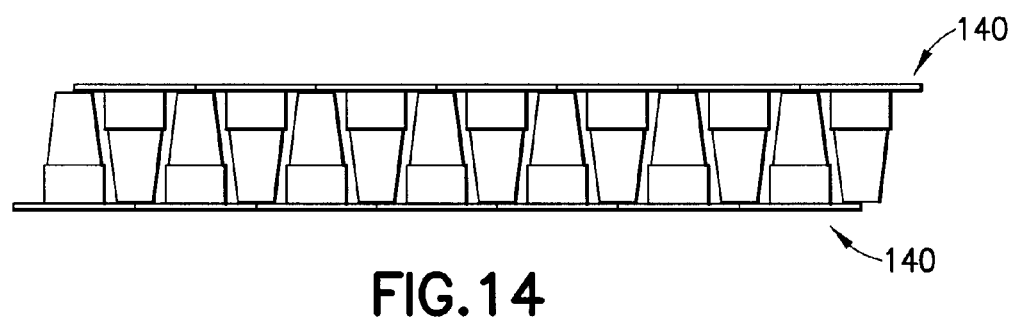

Multiple packaging arrays 140 can then be loaded into a shelf carton. Due to the ability of the packaging arrays 140 to nest (by inverting one of a pair of packaging arrays 140 so that the respective needle portions 112 of the packaging assemblies 100 are adjacent to each other, as shown in FIGS. 13 and 14), utilization of a given space is more efficient. For example, a carton containing 112 packaging assemblies 100 in four nested packaging arrays 140 can be sized approximately ⅓ smaller than a carton containing 100 loose pack outer shields 29. One of ordinary skill in the art will appreciate that other variations of cartons are possible for added patient convenience. As an added manufacturing advantage, the configuration of the packaging arrays 140 allows the packaging arrays 140 to be packaged directly on the assembly line. This eliminates the need to transport sealed pen needles 10 from the assembly line to the packaging line during manufacturing, which is one of the prime contributors to prematurely ruptured seals.

Because of the tight operating window of the process for sealing the teardrop labels 32 to the outer shields 29, failures have been known to occur in the manufacturing process. Though such failures are usually caught and inspected out, the process itself and the required destructive testing contributes to increased waste and reduced efficiency in manufacturing. One advantage of embodiments of the present invention is a manufacturing cost reduction. This cost reduction is due to the decrease in previously required in-process testing, to assure proper sealing of the label 32 to the flange 30. In manufacturing the outer shield 29, the sample size is large and the in-process testing is performed often. With the destructive nature of the test, a large amount of good product is destroyed and the associated cost is not recovered. Because of the more easily achieved conditions for manufacturing the embodiments of the present invention described above, sample sizes can be reduced and/or frequency of testing can be reduced to achieve similar success rates.

An additional advantage of embodiments of the present invention is additional manufacturing savings due to increased efficiency in the use of materials for sterility barriers. In the manufacturing of the outer shield 29, the tear drop labels 32 are held in a web of the same material, with the actual labels 32 representing only about 25-30% of a roll of web material. This means that 70-75% of the label 32 material that is purchased is discarded as scrap after the teardrop labels 32 have been removed from the web. The square shape of the sterility barriers 116 in embodiments of the present invention can be more efficiently manufactured from a roll of material. Not only is the design of the sterility barriers 116 more cost effective, but the design is more environmentally responsible.

Moreover, during the process of sealing the teardrop labels 32 to the outer shields 29, production must be stopped and the high-temperature heater heads required for the sealing must be cleaned multiple times during each manufacturing shift. Additionally the high-temperature heater modules must be regularly replaced. Further, the pressure compliance modules also require a high degree of maintenance. Another advantage of embodiments of the present invention is that the high equipment maintenance costs associated with the process of sealing the teardrop labels 32 to the outer shield 29 is eliminated.

Although only a few embodiments of the present invention have been shown and described, the present invention is not limited to the described embodiments. Instead, it will be appreciated by those skilled in the art that changes may be made to these embodiments without departing from the principles and spirit of the invention as defined in the appended claims and their equivalents.

What is claimed is:

1. A method of storing and dispensing a pen needle for an injection device, the method comprising:
    pressing gripping portions of a hub portion of an outer cover having a pen needle therein, so that internal portions of the hub portion corresponding to the gripping portions directly contact a hub of the pen needle to increase a surface area of contact between the pen needle and the outer cover;
    attaching the injection device to the pen needle hub while pressing the gripping portions; and
    removing the pen needle from the outer cover.

2. The method according to claim 1, wherein attaching the injection device comprises threading the hub of the pen needle onto the injection device; and
    wherein the method further comprises inserting the pen needle into the outer cover; and
    unthreading the injection device from the hub while pressing the gripping portions so that the internal portions of the hub portion contact the hub of the pen needle to increase the surface area contact between the pen needle and the outer cover.

3. The method according to claim 2, further comprising pressing the gripping portions so that the internal portions of the hub portion contact the hub of the pen needle while removing a non-patient needle portion of the pen needle from a septum of the injection device.

4. The method according to claim 1, wherein the internal portions of the hub portion contacting the hub of the pen needle are disposed between internally protruding structures of the hub portion.

* * * * *